(12) United States Patent
Lowe, III

(10) Patent No.: US 6,362,195 B1
(45) Date of Patent: Mar. 26, 2002

(54) BRANCHED ALKOXY-SUBSTITUTED 2-AMINOPYRIDINES AS NOS INHIBITORS

(75) Inventor: John Adams Lowe, III, Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/381,887

(22) PCT Filed: Aug. 11, 1998

(86) PCT No.: PCT/IB98/01223

§ 371 Date: Mar. 28, 2000

§ 102(e) Date: Mar. 28, 2000

(87) PCT Pub. No.: WO99/11620

PCT Pub. Date: Mar. 11, 1999

Related U.S. Application Data

(60) Provisional application No. 60/057,739, filed on Aug. 28, 1997.

(51) Int. Cl.[7] ..................... C07D 401/10; A61K 31/501
(52) U.S. Cl. ..................... 514/307; 514/255; 514/339; 514/304; 514/278; 514/318; 514/343; 544/360; 546/148; 546/276.7; 546/125; 546/19; 546/194; 546/276.4
(58) Field of Search ..................... 544/360; 546/194, 546/276.4, 148, 276.7, 125, 19; 514/255, 318, 343, 307, 339, 304, 278

(56) References Cited

U.S. PATENT DOCUMENTS 5,773,438 A * 10/1999 Levy et al. .................. 514/237
5,972,975 A * 10/1999 Esser et al. .................. 514/352
6,066,642 A * 5/2000 Jacobson .................... 514/267
6,235,747 B1 * 5/2001 Lowe, III et al. ........ 546/276.7

FOREIGN PATENT DOCUMENTS

WO   WO9618616   6/1996
WO   WO9736871   10/1997
WO   WO9824766   6/1998

OTHER PUBLICATIONS

CA 117: 234012, Bender et al., 1992.*

* cited by examiner

Primary Examiner—Jane Fan
(74) Attorney, Agent, or Firm—Peter C. Richardson; Paul H. Ginsburg; E. Victor Donahue

(57) ABSTRACT

The present invention relates to 6-phenyl-pyridin-2-ylamine derivatives of the formula

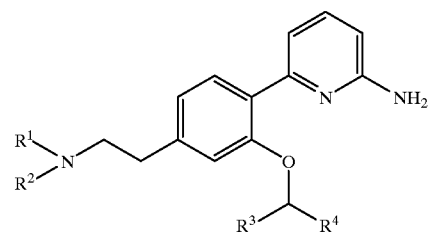

I wherein $R^1$, $R^2$, $R^3$ and $R^4$ are defined as in the specification, that exhibit activity as nitric oxide synthase (NOS) inhibitors, to pharmaceutical compositions containing them and to their use in the treatment and prevention of central nervous system and other disorders.

9 Claims, No Drawings

BRANCHED ALKOXY-SUBSTITUTED 2-AMINOPYRIDINES AS NOS INHIBITORS

The present application represents the United States national stage of International Application PCT/IB98/01223, filed Aug. 11, 1998, and claims priority under 35 USC. section 119 to U.S. provisional application 60/057,739 filed Aug. 28, 1997.

The present invention relates to certain branched alkoxy-subsituted 2-aminopyridines that exhibit activity as nitric oxide synthase (NOS) inhibitors, to pharmaceutical compositions containing them and to their use in the treatment and prevention of central nervous system disorders, inflammatory disorders, septic shock and other disorders.

There are three known isoforms of NOS—an inducible form (I-NOS) and two constitutive forms referred to as, respectively, neuronal NOS (N-NOS) and endothelial NOS (E-NOS). Each of these enzymes carries out the conversion of arginine to citrulline while producing a molecule of nitric oxide (NO) in response to various stimuli. It is believed that excess nitric oxide (NO) production by NOS plays a role in the pathology of a number of disorders and conditions in mammals. For example, NO produced by I-NOS is thought to play a role in diseases that involve systemic hypotension such as toxic shock and therapy with certain cytokines. It has been shown that cancer patients treated with cytokines such as interleukin 1 (IL-1), interleukin, 2 (IL-2) or tumor necrosis factor (TNF) suffer cytokine-induced shock and hypotension due to NO produced from macrophages, i.e., inducible NOS (I-NOS), see *Chemical & Engineering News*, Dec. 20, p. 33, (1993). I-NOS inhibitors can reverse this. It is also believed that I-NOS plays a role in the pathology of diseases of the central nervous system such as ischemia. For example, inhibition of I-NOS has been shown to ameliorate cerebral ischemic damage in rats, see *Am. J. Physiol.*, 268, p. R286 (1995)). Suppression of adjuvant induced arthritis by selective inhibition of I-NOS is reported in *Eur. J. Pharmacol.*, 273, p. 15–24 (1995).

NO produced by N-NOS is thought to play a role in diseases such as cerebral ischemia, pain, and opiate tolerance. For example, inhibition of N-NOS decreases infarct volume after proximal middle cerebral artery occlusion in the rat, see *J. Cerebr. Blood Flow Metab.*, 14 p. 924–929 (1994). N-NOS inhibition has also been shown to be effective in antinociception, as evidenced by activity in the late phase of the formalin-induced hindpaw licking and acetic acid-induced abdominal constriction assays, see *Br. J. Pharmacol.*, 110, p. 219–224 (1993). Finally, opioid withdrawal in rodents has been reported to be reduced by N-NOS inhibition, see *Neuropsychopharmacol.*, 13, p. 269–293 (1995).

SUMMARY OF THE INVENTION

This invention relates to compounds of the formula

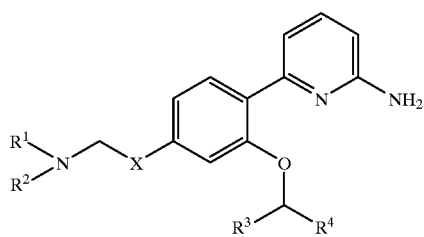

I wherein X is CHOH; $CH_2$; or $CHR^{10}$, wherein $R^{10}$ (ethylene or n-propylene), together with the CH of $CHR^{10}$, the adjacent $CH_2$ group, and the nitrogen of $NR^1R^2$, forms a five or six membered saturated ring, in which case $R^2$ is a single bond;

$R^1$, $R^2$ (when X is not $CHR^{10}$), $R^3$ and $R^4$ are selected, independently, from ($C_1$–$C_6$) alkyl, tetrahydronaphthalene, aryl and aralkyl, wherein said aryl and the aryl moiety of said aralkyl is phenyl or naphthyl and the alkyl moiety is straight or branched and contains from 1 to 6 carbon atoms, and wherein said ($C_1$–$C_6$) alkyl and said tetrahydronaphthalene and the aryl moiety of said aralkyl may optionally be substituted with from one to three substituents, preferably from zero to two substituents, that are selected, independently, from halo (e.g., chloro, fluoro, bromo, iodo), nitro, hydroxy, cyano, amino, ($C_1$–$C_4$) alkoxy, and ($C_1$–$C_4$) alkylamino;

or $R^1$ and $R^2$ (when X is not $CHR^{10}$), together with the nitrogen to which they are attached, form a piperazine, piperidine or pyrolidine ring or a azabicyclic ring containing from 6 to 14 ring members, from 1 to 3 of which are nitrogen and the rest of which are carbon, wherein examples of said azabicyclic rings are the following

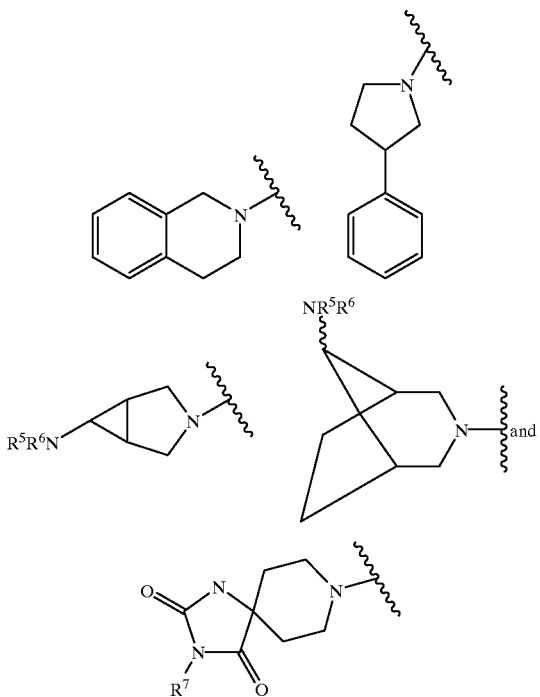

wherein $R^5$ and $R^6$ are selected from hydrogen, ($C_1$–$C_6$) alkyl, phenyl, naphthyl, ($C_1$–$C_6$)alkyl-C(=O)—, HC(=O)—, ($C_1$–$C_6$)alkoxy-(C=O)—, phenyl-C(=O)—, naphthyl-C(=O)—, and $R^8R^9NC(=O)$— wherein $R^8$ and $R^9$ are selected, independently, from hydrogen and ($C_1$–$C_6$)alkyl;

$R^7$ is selected from hydrogen, ($C_1$–$C_6$)alkyl, phenyl, naphthyl, phenyl-($C_1$–$C_6$)alkyl- and naphthyl($C_1$–$C_6$) alkyl-;

and wherein said piperazine, piperidine and pyrrolidine rings may optionally be substituted with one or more substituents, preferably with from zero to two substituents that are selected, independently, from ($C_1$–$C_6$) alkyl, amino, ($C_1$–$C_6$) alkylamino, [di-($C_1$–$C_6$)alkyl] amino, phenyl substituted 5 to 6 membered heterocyclic rings containing from 1 to 4 rings nitrogen atoms, benzoyl, benzoylmethyl, benzylcarbonyl, phenylaminocarbonyl, phenylethyl and phenoxycarbonyl, and wherein the phenyl moieties of any of the foregoing substituents may optionally be substituted with one or more substituents, preferably with from zero to two substituents, that are selected, independently, from halo, $(C_1-C_3)$alkyl, $(C_1-C_3)$ alkoxy, nitro, amino, cyano, $CF_3$ and $OCF_3$;

and wherein $R^3$ and $R^4$, together with the carbon to which they are attached, form an optionally substituted carbocyclic ring of from 3 to 8 members;

and the pharmaceutically acceptable salts of such compounds.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinatate, maleate, fumarate, gluconate, saccharate, benzoate, methanesulfonate, ethanesulfonate, benzenesulfonate, p-toluenesulfonate and pamoate [i.e., 1,1-methylene-bis-(2-hydroxy-3-naphthoate)] salts.

The term "alkyl", as used herein, unless otherwise indicated, includes saturated monovalent hydrocarbon radicals having straight, branched or cyclic moieties or combinations thereof.

The term "one or more substituents", as used herein, refers to a number of substituents that equals from one to the maximum number of substituents possible based on the number of available bonding sites.

The terms "halo" and "halogen", as used herein, unless otherwise indicated, include chloro, fluoro, bromo and iodo.

More specific embodiments of the present invention include:

(a) compounds of the formula I wherein $R^1$, $R^2$, $R^3$ and $R^4$ are selected, independently, from $(C_1-C_6)$alkyl;

(b) compounds of the formula I wherein $R^3$ and $R^4$ are selected, independently, from $(C_1-C_6)$alkyl, and $R^1$ and $R^2$, together with the nitrogen to which they are attached, form a ring;

(c) compounds of the formula I wherein one of $R^1$ and $R^2$ is selected from $(C_1-C_6)$alkyl, and the other is selected from phenyl or phenyl-$(C_1-C_6)$alkyl;

(d) compounds of the formula I wherein $R^1$ and $R^2$, together with the nitrogen to which they are attached, form a piperazine, piperidine or pyrrolidine ring; and (e) compounds of the formula I wherein $R^1$ and $R^2$ are selected, independently from $(C_1-C_6)$alkyl, and $R^3$ and $R^4$, together with the carbon to which they are attached, form a ring.

Examples of specific preferred embodiments of this invention are:

6-[2-Isopropoxy-4-((4-phenethylpiperazin-1-yl)-ethyl)-phenyl]-pyridin-2-ylamine;

6-[2-Isobutoxy-4-((4-phenethylpiperazin-1-yl)-ethyl)-phenyl]-pyridin-2-ylamine;

6-[2-Isobutoxy-4-((4-dimethylaminoethyl)-phenyl]-pyridin-2-ylamine;

6-[2-Isopropoxy-(N-(2-methyl)propyl)-4-(pyrrolidin-3-yl)-phenyl]-pyridin-2-ylamine;

1-[4-(6-Amino-pyridin-2-y)-3-isopropoxy-phenyl]-2-(4-phenethyl-piperazin-1-yl)-ethanol;

6-[2-Cyclopentyloxy-4-((4-dimethylaminoethyl)-phenyl]-pyridin-2-ylamine;

6-[2-Cyclopentyloxy-4-((4-phenethylpiperazin-1-yl)-ethyl)-phenyl]-pyridin-2-ylamine; and the pharamaceutically acceptable salts of the foregoing compounds.

Other examples of specific embodiments of this invention are:

6-[2-Cyclohexyloxy-4-((4-phenethylpiperazin-1-yl)-ethyl)-phenyl]-pyridin-2-ylamine;

6-[2-Cyclobutyloxy-4-((4-phenethylpiperazin-1-yl)-ethyl)-phenyl]-pyridin-2-ylamine;

6-[2-Cyclopropyloxy-4-((4-phenethylpiperazin-1-yl)-ethyl)-phenyl]-pyridin-2-ylamine;

6-[2-Isopentyloxy-4-((4-phenethylpiperazin-1-yl)-ethyl)-phenyl]-pyridin-2-ylamine;

6-[2-Isohexyloxy-4-((4-phenethylpiperazin-1-yl)-ethyl)-phenyl]-pyridin-2-ylamine;

6-[2-Cyclopentyloxy-(N-(2-methyl)propyl)-4-(pyrrolidin-3-yl)-phenyl]-pyridin-2-ylamine;

6-[2-Cyclohexyloxy-(N-(2-methyl)propyl)-4-(pyrrolidin-3-yl)-phenyl]-pyridin-2-ylamine;

6-[2-Cyclobutyloxy-(N-(2-methyl)propyl)-4-(pyrrolidin-3-yl)-phenyl]-pyridin-2-ylamine;

6-[2-Cyclopropyloxy-(N-(2-methyl)propyl)-4-(pyrrolidin-3-yl)-phenyl]-pyridin-2-ylamine, 6-[2-Isopentyloxy-(N-(2-methyl)propyl)-4-(pyrrolidin-3-yl)-phenyl]-pyridin-2-ylamine;

6-[2-Isohexyloxy-(N-(2-methyl)propyl)-4-(pyrrolidin-3-yl)-phenyl]-pyrdin-2-ylamine;

1-[4-(6-Aminopyrdin-2-yl)-3-isobutoxy-phenyl]-2-(4-phenethyl-piperazin-1-yl)-ethanol;

1-[4-(6-Amino-pyridin-2-yl)-3-isopropoxy-phenyl]-2-(6,7-dimethoxy-tetrahydroisoquinol-2-yl)-ethanol;

1-[4-(6-Amino-pyridin-2-yl)-3-isopropoxy-phenyl]-2-(4-dimethylamino-piperidin-1-yl)-ethanol;

1-[4-(6-Amino-pyridin-2-yl)-3-isopropoxy-phenyl]-2-(dimethylamino)-ethanol; and

1-[4-(6-Amino-pyridin-2-yl)-3-cyclopenyloxy-phenyl]-2-(4-phenethyl-piperazin-1-yl)-ethanol;

and the pharmaceutically acceptable salts of the foregoing compounds.

The present invention also relates to a pharmaceutical composition for treating or preventing a condition selected from the group consisting of migraine, inflammatory diseases (e.g., asthma and psoriasis), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, Parkinson's disease, chemical dependencies and addictions, emesis, epilepsy, anxiety, psychosis, depression, (e.g., major depressive disorder and dysthymia), head trauma, adult respiratory distress syndrome (ARDS), morphine induced tolerance and withdrawal symptoms, inflammatory bowel disease, osteoarthrits, rheumatoid arthritis, ovulation, dilated cardiomyopathy, acute spinal cord injury, Huntington's disease, glaucoma, macular degeneration, diabetic neuropathy, diabetic nephropathy and cancer in a mammal, including a human, comprising an amount of a compound of the formula I, or a pharmaceutically acceptable salt thereof that is effective in treating or preventing such condition, and a pharmaceutically acceptable carrier.

The present invention also relates to a method of treating or preventing a condition selected from the group consisting of migraine, inflammatory diseases (e.g., asthma and psoriasis), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol and nicotine), Parkinson's disease, emesis, epilepsy, anxiety, psychosis, depression, (e.g., major depressive disorder and dysthymia), head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, glaucoma, macular degeneration, diabetic neuropathy, diabetic nephropathy and cancer in a mammal, including a human, comprising administering to said mammal an amount of a compound of the formula I, or a pharmaceutically acceptable salt thereof, that is effective in treating or preventing such condition.

The present invention also relates to a pharmaceutical composition for inhibiting nitric oxide synthase (NOS) in a mammal, including a human, comprising an NOS inhibiting effective amount of a compound of the formula I, or a pharmaceutically acceptable salt thereof and a pharmaceutically acceptable carrier.

The present invention also relates to a method of inhibiting NOS in a mammal, including a human, comprising administering to said mammal a NOS inhibiting effective amount of a compound of the formula I, or a pharmaceutically acceptable salt thereof.

The present invention also relates to a pharmaceutical composition for treating or preventing a condition selected from the group consisting of migraine, inflammatory diseases (e.g., asthma and psoriasis), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol and nicotine), Parkinson's disease, emesis, epilepsy, anxiety, psychosis, depression, (e.g., major depressive disorder and dysthymia), head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntingting's disease, glaucoma, macular degeneration, diabetic neuropathy, diabetic nephropathy and cancer in a mammal, including a human, comprising a NOS inhibiting effective amount of a compound of the formula I, or a pharmaceutically acceptable salt thereof and a pharmaceutically acceptable carrier.

The present invention also relates to a method of treating or preventing a condition selected from the group consisting of migraine, inflammatory diseases (e.g., asthma and psoriasis), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol or nicotine), Parkinson's disease, emesis, epilepsy, anxiety, psychosis, depression, (e.g., major depressive disorder and dysthymia), head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, glaucoma, macular degeneration, diabetic neuropathy, diabetic nephropathy and cancer in a mammal, including a human, comprising administering to said mammal a NOS inhibiting effective amount of a compound of the formula I, or a pharmaceutically acceptable salt thereof.

Compounds of formula I have chiral centers and therefore may exist in diffenent enantiomeric and diastereomeric forms. This invention relates to all optical isomers and all stereoisomers of compounds of the formula I and mixtures thereof, and to all pharmaceutical compositions and methods of treatment defined above that contain or employ them, respectively.

Formula I above includes compounds identical to those depicted but for the fact that one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

The compounds of the formula I may be prepared as described in the following reaction schemes and discussion. Unless otherwise indicated, X, $R^1$, $R^2$, $R^3$, $R^4$, $R^5$, $R^6$, $R^7$, $R^8$, $R^9$ and $R^{10}$ and structural formula I in the reaction schemes and discussion that follow are defined as above.

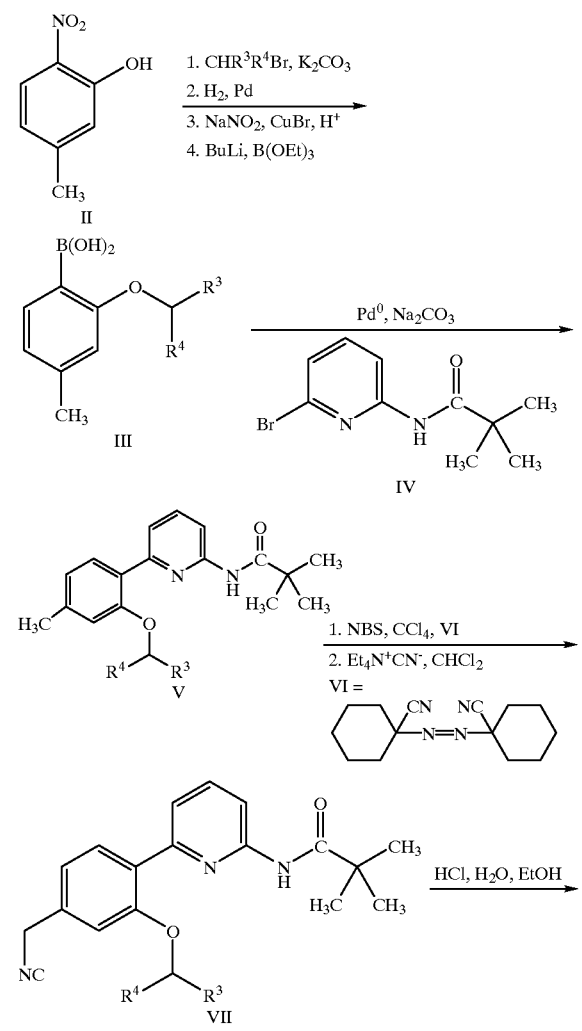

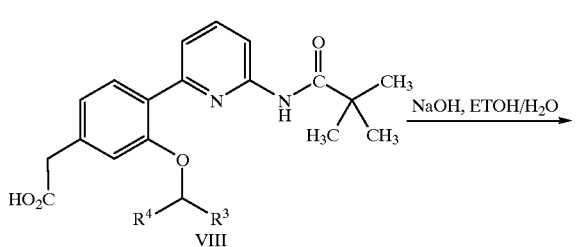

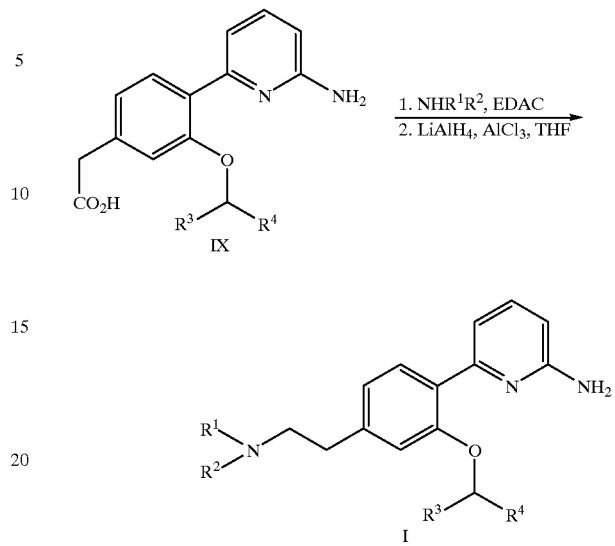

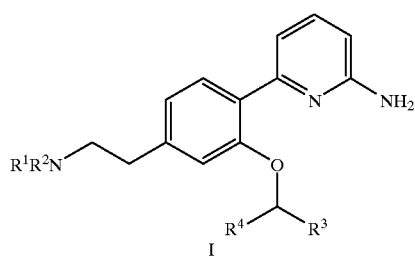

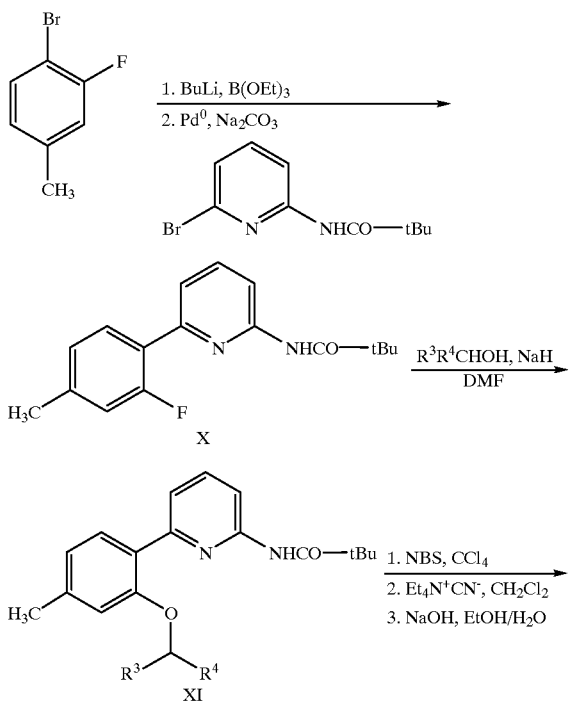

Referring to Scheme 1, the compound of formula II is reacted with a compound of the formula $CHR^3R^4Br$ or $CHR^2R^4I$ and potassium carbonate, in a solvent such as acetonitrile, at about the reflux temperature of the reaction mixture, to convert the hydroxy group of formula II into a group having the formula —$OCHR^3R^4$. The resulting compound is then reduced, at about room temperature, using hydrogen gas in the presence of 10% palladium on carbon, in an ethanol solvent, to form 3-$OCHR^3R^4$-4-aminotoluene, which is then reacted with sodium nitrite and cuprous bromide in concentrated sulfuric acid to form 3-$OCHR^3R^4$-4-bromotoluene.

The 3-$OCHR^3R^4$-4-bromotoluene produced in the foregoing reaction is then cooled to about $-70°$ C. in dry tetrahydrofuran (THF), and a solution of n-butyl lithium is added to it. The resulting solution is then treated with triethyl borate and allowed to warm to room temperature to form the compound of formula III.

The compound of formula III is reacted with the compound of formula IV to form the compound of formula V. This reaction is generally carried out in an aqueous ethanol solvent, in the presence of sodium carbonate and tetrakistriphenylphosphine palladium, at about the reflux temperature of the reaction mixture.

The compound of the formula VII can be formed in the following manner. First, the compound of formula V is reacted with N-bromosuccinimide (NBS) and bis-(1-cyano-1-aza)-cyclohexane (formula VI) in carbon tetrachloride and refluxed for about 8 hours, with additional portions of the initiator being added at about 1, 2 and 4 hours. After evaporation of the solvent, the product of this reaction is reacted with triethylammonium cyanide in methylene chloride at about room temperature to form the compound of formula VII.

Saturation of a solution of the compound of formula VII in ethanol with hydrogen chloride, followed by refluxing the mixture and then heating in aqueous hydrochloric acid, yields the compound of formula VII. Hydrolysis of the compound of formula VII yields the corresponding compound of formula IX. The base hydrolysis is typically carried out using an alkali metal or alkaline earth metal hydroxide in a mixture of ethanol and water at a temperature from about room temperature to about the reflux temperature of the solvent.

The compound of the formula IX that is formed in the preceding step can be converted into the compound of formula I in the following manner. First, the compound of formula IX is reacted with the appropriate compound of the formula $R^2R^1NH$ and N-ethyl-N-dimethylaminopropyl carbodiimide (EDAC) in the presence of a base. Examples of suitable bases are those selected from trialkylamines, alkali metal carbonates and alkaline earth metal carbonates. This reaction is typically conducted in a solvent such as acetonitrile, methylene chloride or N,N-dimethylformamide (DMF), at a temperature from about room temperature to about 100° C., preferably at about room temperature. Preferably, the reaction is conducted in the presence of a catalytic additive such as N-hydroxysuccinamide or hydroxybenzotriazole.

The product of the foregoing reaction is then reduced using methods well known to those of skill in the art. For example, the reduction can be carried out using lithium aluminum hydride in tetrahydrofuran, with or without aluminum chloride, or using borane methyl sulfide in tetrahydrofuran, at a temperature of about −78° C. to about 0° C., preferably at about −70° C., to yield the desired compound of formula I.

Referring to Scheme 2, 4-bromo-3-fluorotoluene is first converted to the boronic acid derivative and then coupled to 6-bromo-2-(t-butylcarbonylamino)pyridine to form compound of the formula X in the following manner. A halogen-metal exchange reaction is carried out on 3-fluoro4-bromotoluene in tetrahydrofuran, ether, dimethoxyethane, hexane or another suitable ethereal or hydrocarbon solvent, at a temperature from −100° C. to about room temperature, using butyl lithium or another suitable alkyl lithium reagent, followed by reaction with a borate triester such as triethyl or triisopropyl borate, for about 1 to about 48 hours at a temperature from about −100° C. to about the reflux temperature. The intermediate boronic acid derivative is then converted into the compound of formula X in an aqueous ethanol solvent, in the presence of sodium carbonate and tetrakistriphenylphosphine palladium, at about the reflux temperature of the reaction mixture, using 6-bromo-2-(t-buylcarbonylamino)pyridine as the coupling partner. The compound of formula X is then converted into a compound of the formula XI by displacement of the fluoro group from the alcohol with a suitable alkoxide, which is formed in a solvent such as dimethylformamide, tetrahydrofuran or dioxane, and a metal hydride such as sodium hydride, at a temperature from about room temperature to about the reflux temperature, for a period of about 5 minutes to about 5 hours. The reaction with the compound of formula X is carried out in this reaction system at a temperature from room temperature to about the reflux temperature for a period from about 1 to about 48 hours.

The compound of formula XI is then converted into the corresponding compound of the formula IX in the following manner. First, the compound of formula XI is reacted with N-bromosuccinimide (NBS) and bis-(1-cyano-1-aza)-cyclohexane (formula VI in Scheme 1) in carbon tetrachloride and refluxed for about 8 hours, with additional portions of the initiator being added after about 1, 2 and 4 hours, to brominate the methyl group of such compound. After evaporation of the solvent, the product of this reaction is reacted with triethylammonium cyanide in methylene chloride at about room temperature to form the corresponding compound wherein the bromo substituent is replaced by cyano.

The resulting cyano derivative is then hydrolyzed to form the corresponding compound of formula IX. The base hydrolysis is typically carried out using an alkali metal or alkaline earth metal hydroxide in a mixture of ethanol and water at a temperature from about room temperature to about the reflux temperature of the solvent.

The compound of the formula IX that is formed in the preceding step can be converted into the compound of formula I in the following manner. First, the compound of formula IX is reacted with the appropriate compound of the formula $R^2R^1NH$ and N-ethyl-N-dimethylaminopropyl carbodiimide (EDAC) in the presence of a base. Examples of suitable bases are those selected from trialkylamines, alkali metal carbonates and alkaline earth metal carbonates. This reaction is typically conducted in a solvent such as acetonitrile, methylene chloride or N,N-dimethylformamide (DMF), at a temperature from about room temperature to about 100° C., preferably at about room temperature. Preferably, the reaction is conducted in the presence of a catalytic additive such as N-hydroxysuccinamide or hydroxybenzotriazole.

The product of the foregoing reaction is then reduced using methods well known to those of skill in the art to yield the desired compound of formula I. For example, the reduction can be carried out using lithium aluminum hydride in tetrahydrofuran, with or without aluminum chloride, or using borane methyl sulfide in tetrahydrofuran, at a temperature of about −78° C. to about 0° C., preferably at about −70° C.

Compounds of the formula I wherein X is CHOH can be prepared using a procedure analogous to that described in Example 7 of this application. Compounds of the formula I wherein X is part of a five or six membered saturated ring may be prepared using a procedure analogous to that described in Example 6.

The starting materials used in the procedures of Schemes 1 and 2 are either commercially available, known in the art or readily obtainable form known compounds by methods that will be apparent to those skilled in the art.

The preparation of other compounds of the formula I not specifically described in the foregoing experimental section can be accomplished using combinations of the reactions described above that will be apparent to those skilled in the art.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of formulae I ("the active compounds of this invention") which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid additon salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The active compounds of this invention and their pharmaceutically acceptable salts are useful as NOS inhibitors i.e., they possess the ability to inhibit the NOS enzyme in mammals, and therefore they are able to function as therapeutic agents in the treatment of the aforementioned disorders and diseases in an afflicted mammal.

The active compounds of this invention and their pharmaceutically acceptable salts can be administered via either the oral, parenteral or topical routes. In general, these compounds are most desirably administered in dosages ranging from about 0.01 to about 250 mg per day, in single or divided doses (i.e., from 1 to 4 doses per day), although variations will necessarily occur depending upon the species, weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The active compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically when treating inflammatory conditions of the skin and this may be done by way of creams, jellies, gels, pastes, patches, ointments and the like, in accordance with standard pharmaceutical practice.

The ability of compounds of the formulae I to inhibit NOS may be determined using procedures described in the literature. The ability of compounds of the formulae I to inhibit endothelial NOS may be determined by using the procedures described by Schmidt et al. in *Proc. Natl. Acad. Sci. U.S.A.*, 88, pp. 365–369 (1991) and by Pollock et al., in *Proc. Natl. Acad. Sci. U.S.A.*, 88, pp. 10480–10484 (1991). The ability of compounds of the formulae I to inhibit inducible NOS may be determined using the procedures described by Schmidt et al., in *Proc. Natl. Acad, Sci. U.S.A.*, 88 pp. 365–369 (1991) and by Garvey et al. in *J. Biol. Chem.*, 269, pp. 26669–26676 (1994). The ability of the compounds of the formulae I to inhibit neuronal NOS may be determined using the procedure described by Bredt and Snyder in *Proc. Natl. Acad. Sci. U.S.A.*, 87, 682–685 (1990).

The title compound of Example 1 below exhibited an $IC_{50}<10$ $\mu M$ for inhibition of either inducible or neuronal NOS.

The present invention is illustrated by the following examples. It will be understood, however, that the invention is not limited to the specific details of these examples. Melting points are uncorrected. Proton nuclear magnetic resonance spectra ($^1H$ NMR) and $C^{13}$ nuclear magnetic resonance spectra were measured for solutions in deuterochloroform ($CDCl_3$) or in $CD_3OD$ or $CD_3SOCD_3$ and peak, positions are expressed in parts per million (ppm) downfield from tetramethylsilane (TMS). The peak shapes are denoted as follows: s, singlet; d, doublet; t, triplet; q, quartet, m, multiplet, b, broad.

EXAMPLE 1

6-[2-METHOXY-4-((4-PHENETHYLPIPERAZIN-1-YL)-ETHYL)-PHENYL]-PYRIDIN-2-YLAMINE

A. 2-Isopropoxy-4-bromo-nitrobenzene

To a 500 mL round-bottomed flask equipped with condenser and $N_2$ inlet were added 20 g (130 mmol) 2-nitro-5-methylphenol, 29.6 mL (260 mmol) isopropyl iodide, 35.9 g (260 mmol) potassium carbonate, and 250 mL dry acetonitrile. The reaction was refluxed 24 hours, cooled and concentrated. The residue was taken up in 1 N aqueous sodium hydroxide solution and extracted into methylene choride. The organic layer washed with brine, dried over sodium, and evaporated. The residue, 21.4 g (84%) was used directly in the next step.

$^1$H-NMR ($CDCl_3$, δ): 1.35 (δ, J=6, 6H), 2.36 (s, 3H), 4.63 (m, J=6, 1H), 6.75 (d, J=8, 1H), 6.84 (s, 1H), 7.68 (d, J=8, 1H).

$^{13}$C-NMR (CDCl$_3$, δ): 21.9, 72.5, 116.7, 120.9, 125.6, 145.2, 151.5.

APCI MS (%): 196 (parent+1, 100).

The oil was taken up in 200 mL ethanol and treated with 45 p.s.i. hydrogen in the presence of 10% palladium-on-carbon for 12 hours, then filtered through Celite and concentrated to afford an oil, 16.4 g (90%).

$^1$H-NMR (CDCl$_3$, δ): 1.345 (d, J=6, 6H), 2.25 (s, 3H), 3.65 (bs, 2H), 4.51 (m, J=6, 1H), 6.6 (m, 3H).

$^{13}$C-NMR (CDCl$_3$, δ): 21.0, 22.4, 370.6, 114.7, 115.3, 121.3, 127.9, 134.7, 145.4.

APCI MS (%): 166 (parent+1, 100).

B. 3-Isopropoxy-4-bromotoluene

To a 250 mL round-bottomed flask equipped with condenser and N$_2$ inlet were added 14.4 g (87.1 mmol) 3-isopropoxy-4-aminotoluene, 94 mL water, and 15 mL concentrated sulfuric acid. The solution was cooled to 0° C., and a solution of 6.9 g (100 mmol) sodium nitrite in 29 mL water was added dropwise over 5 minutes, and stirring continued for 10 minutes. The tan solution was then added slowly to a slurry of 25 g (170 mmol) cuprous bromide in 18 mL concentrated sulfuric acid heated to 90° C., and the reaction stirred at 80° C. for 2 hours. It was then cooled, poured into water, and extracted with methylene chloride. The methylene chloride layer was washed with 1 N aqueous sodium hydroxide solution, water, and brine, dried over sodium sulfate, and evaporated to an oil, which was chromatographed on silica gel using hexane/ethyl acetate as eluant to afford the product as an oil, 3.59 g (18%).

$^1$H-NMR (CDCl$_3$, δ): 1.35 (d, J=6, 6H), 2.28 (s, 3H), 4.51 (m, J=6, 1H), 6.62 (d, J=7, 1H), 6.72 (s, 1H), 7.36 (d, J=7, 1H).

APCI MS (%): 228/230 (parent+1, 100/98).

C. 2-Isopropoxy-4-methylphenylboronic Acid

To a 125 mL 3N round-bottomed flask equipped with N$_2$ inlet and septum were added 3.59 g (15.7 mmol) 3-isopropoxy-4-bromotoluene and 30 mL dry tetrahydrofuran. The solution was cooled to −70° C. and 7.5 mL (18.8 mmol) of a 2.5 M solution of butyl lithium in hexane was added over 5 minutes, and the solution stirred 5 minutes at −70° C. Then 3.2 mL (18.8 mmol) triethyl borate was added, followed by stirring for 5 minutes at −70° C. and then stirring at room temperature for 24 hours. The reaction was quenched with 1 N aqueous hydrochloric acid and extracted into ethyl acetate. The organic layer was washed with water and brine, dried over sodium sulfate, and evaporated. The residue was triturated with hexane to a white solid, 1.7 g (56%).

$^1$H-NMR (CDCl$_3$, δ): 1.39 (d, J=6, 6H), 2.35 (s, 3H), 4.69 (m, J=6, 1H), 6.25 (s, 2H), 6.71 (s, 1H), 6.81 (d, J=7, 1H), 7.70 (d, J=7, 1H).

D. N-t-Butylcarbonyl-6-(2-isopropoxy-4-methylphenyl)-pyridin-2-ylamine

To a 125 mLL round-bottomed flask equipped with condenser and N$_2$ inlet were added 3.3 g (16 mmol) 6-bromo-2-(t-butylcarboxamido)-pyridine, 3.1 g (12.8 mmol) 2-isopropoxy-4-methylphenylboronic acid, 6.8 g (640 mmol) sodium carbonate, 462 mg (0.4 mmol) tetrakistriphenylphosphine palladium, 30 mL ethanol, and 3 mL water. The mixture was refluxed 16 hours, cooled, poured into water, and extracted into ethyl acetate. The organic layer was washed with brine, dried over sodium sulfate, and evaporated. The residue was chromatographed on silica gel using hexanelethyl acetate as eluant to afford 4.3 g (100%) of an oil.

$^1$H-NMR (CDCl$_3$, δ): 1.27 (d, J=6, 6H), 1.31 (s, 9H), 2.36 (s, 3H), 4.49 (m, 1H), 6.795 (s, 1H), 6.85 (d, J=8, 1H), 7.60 (m, 2H), 7.65 (t, J=8, 1H), 8.10 (bs, 1H), 8.12 (d, J=8, 1H).

$^{13}$C-NMR (CDCl$_3$, δ): 21.5, 11.0, 237.4, 39.7, 371.0, 111.3, 115.8, 121.1, 121.8. 126.9, 130.7, 13.6, 140.0, 151.0, 154.5, 155.2, 176.9.

APCI MS (%): 327 (parent+1, 100).

E. N-t-Butylcarbonyl-6-(2-isopropoxy-4-cyanomethylphenyl)-pyridin-2-ylamine

To a 250 mL round-bottomed flask equipped with condenser and N$_2$ inlet were added 4.1 g (12.6 mmol) N-t-butylcarbonyl-2-isopropoxy-4-methylphenyl)-pyridin-2-ylamine, 2.7 g (15.1 mmol) N-bromosuccinimide, 150 mL carbon tetrachloride, and 80 mg bis-(1-cyano-1 -azo)-cyclohexane. The reaction was heated at reflux for a total of 8 hours as additional portions of initiator were added at 1 and 2 hours. The reaction was cooled, filtered with carbon tetrachloride, and evaporated. The red oil was used directly.

$^1$H-NMR (δ, CDCl$_3$): 1.30 (d, J=6, 6H), 1.32 (s, 9H), 4.50 (s, 2H), 4.55 (m, J=6, 1H), 7.00 (s, 1H), 7.06 (d, J=8, 1H), 7.6–7.7 (m, 3H), 8.04 (bs, 1H), 8.15 (d, J=8, 1H).

MS (%): 405/407 (parent+1, 98/100). The above oil was taken up in 150 mL dry methylene chloride and treated with 1.9 g (1.26 mmol) tetraethylammonium cyanide, and reaction stirred at room temperature for 13 hours. LCMS showed a major peak at P+1=352 and TLC showed a major spot at R$_f$=0.4 in 20% ethyl acetate in hexane. The reaction was evaporated, and the residue chromatographed on silica gel using ethyl acetate in methylene chloride as eluant to afford 328 mg (7%) of a foam.

$^1$H-NMR (δ, CDCl$_3$): 1.30 (d, J=6, 6H), 1.33 (s, 9H), 3.77 (s, 2H), 4.58 (m, 1H), 6.95 (s, 1H), 6.985 (d, J=8, 1H), 7.5–7.8 (m, 3H), 8.04 (bs, 1H), 8.16 (d, J=8, 1H).

$^{13}$C-NMR (δ, CDCl$_3$): 22.0, 23.6, 27.5, 39.8, 71.4, 112.0, 114.15, 120.4, 121.2, 129.4, 131.5, 131.8, 137.9, 151.1, 153.6, 155.9, 177.1.

MS (%): 352 (parent+1, 100).

F. N-t-Butylcarbonyl-6-(2-isopropoxy-4-carboethoxymethylphenyl)-pyridin-2-ylamine To a 100 mL round-bottomed flask equipped with condenser and N$_2$ inlet were added 730 mg (2.09 mmol) N-t-butylcarbonyl-6-(2-isopropoxy-4-cyanomethylphenyl)-pyridin-2-ylamine and 20 mL ethanol. The solution was saturated with HCl, heated to reflux, one drop of water added, and the reaction refluxed 14 hours. The reaction was cooled and concentrated, and the residue taken up in methylene chloride, washed with aqueous sodium hydroxide and water, dried over sodium sulfate, and evaporated to afford 683 mg (82%) of an oil.

$^1$H-NMR (δ, CDCl$_3$): 1.21 (t, J=7, 3H), 1.24 (d, J=6, 6H), 1.27 (s, 9H), 3.58 (s, 2H), 4.11 (q, J=7, 2H), 4.50 (m, J=6, 1H), 6.90 (m, 2H), 7.5–7.7 (m, 3H), 8.11 (d, J=8, 1H), 8.18 (bs, 1H).

$^{13}$C-NMR (δ, CDCl$_3$): 14.2, 22.0, 27.5, 39.8, 41.5, 60.9, 71.0, 111.8, 115.7, 121.2, 121.8, 128.3, 131.1, 136.0, 137.8, 151.1, 154.2, 155.4, 171.3, 177.1.

MS (%): 399 (parent+1, 100).

G. 6-(2-Isopropoxy-4-carboxymethylphenyl)-pyridin-2-ylamine

To a 100 mL round-bottomed flask equipped with condenser and N$_2$ inlet were added 577 mg (1.56 mmol) N-t-butylcarbonyl-6-(2-isopropoxy-4-carboethoxymethylphenyl)-pyridin-2-ylamine and 10 mL ethanol. The solution was heated to reflux, and 30 mL of a 10% aqueous sodium hydroxide solution added dropwise, and refluxing continued for 1 hour. The solution was cooled, and the pH adjusted at 0° C. with 1 N hydrochloric acid to pH 4–5, then extracted with methylene chloride, ethyl acetate, and acetonitrile/ethyl acetate. The combined organic layers were dried and evaporated to give a foam, 449 mg (98%).

$^1$H-NMR (δ, CDCl$_3$): 1.22 (d, J=6, 6H), 3.69 (s, 2H), 4.47 (m, J=6, 1H), 6.59 (d, J=7, 1H), 6.71 (m, 1H), 6.78 (d, J=8, 1H), 6.83 (s, 1H), 7.00 (m, 1H), 7.50 (t, J=8, 1H).

$^{13}$C-NMR (δ, CDCl$_3$): 21.9, 43.9, 71.2, 111.7, 112.1, 115.8, 120.0, 122.7, 130.0, 141.3, 142.0, 144.3, 155.0, 184.4.

MS (%): 287 (parent+1, 100).

H. 6-(2-Isopropoxy-4-N-(4-phenethylpiperazin-1-yl) carboxamidomethylphenyl)-pyrdrin-2-ylamine To a 100 mL round-bottomed flask equipped with condenser and N$_2$ inlet were added 200 mg (0.7 mmol) 6-(2-isopropoxy-4-carboxymethylphenyl)-pyridin-2-ylamine, 266 mg (1.4 mmol) N-phenethylpiperazine, 537 mg (2.8 mmol) N-ethyl, N-3-dimethylaminopropylcarbodiimide, 512 mg (4.2 mmol) N,N-dimethyl-4-aminopyridine, and 10 mL dry dimethylformamide. The reaction was stirred at room temperature 12 hours (LCMS showed P+1=451 and TLC showed R$_f$=0.2 in 5% methanol/methylene chloride), then poured into water, extracted into ethyl acetate, and the organic layer washed with water and brine, dried over sodium sulfate, and evaporated. The residue was chromatographed on silica gel using methanol/methylene chloride as eluant to afford the product as a foam, 180 mg (56%).

$^1$H-NMR (δ, CDCl$_3$): 1.24 (d, J=6, 6H), 2.30 (m, 2H), 2.44 (m, 2H), 2.53 (m, 2H), 2.73 (m, 2H), 3.43 (m, 2H), 3.66 (m, 2H), 3.72 (s, 2H), 4.48 (m, 1H), 4.5 (bs, 2H), 6.38 (d, J=8, 1H), 6.86 (m, 2H), 7.1–7.3 (m, 6H), 7.40 (t, J=8, 1H), 7.69 (d, J=8, 1H).

$^{13}$C-NMR (δ, CDCl$_3$): 22.1, 33.4, 41.2, 41.375, 46.1, 52.7, 53.1, 60.1, 71.2, 106.6, 115.2, 115.6, 121.2, 126.1, 128.4, 128.6, 129.2, 131.4, 136.3, 137.3, 140.0, 154.1, 155.6, 158.0, 169.3.

MS (%): 459 (parent+1, 100).

I. 6-[2-Isopropoxy-4-((4-phenethylpiperazin-1-yl)-ethyl)-phenyl]-pyridin-2-ylamine To a 100 mL round-bottomed flask equipped with condenser and N$_2$ inlet were added 157 mg aluminum chloride and 10 mL dry tetrahydrofuran. The solution was cooled to 0° C., and 2.70 mL (2.70 mmol) of a 1.0 M solution of lithium aluminum hydride in tetrahydrofuran was added. Stirring was continued at room temperature for 20 minutes, then the solution was cooled to –70° C., and a solution of 180 mg (0.39 mmol) 6-(2-isopropoxy-4-N-(4-phenthylpiperazin-1-yl)carboxamidomethylphenyl)-pyridin-2-ylamine in 10 mL dry tetrahydrofuran was added. Stirring was continued 1 hour at –70° C., then 2.5 hours at room temperature (LCMS showed P+1=445), followed by careful quenching with 5 mL 1 N hydrochloric acid. After stirring for 20 minutes, the reaction was treated with 6 mL 6 N aqueous sodium hydroxide solution, and extracted with several portions of methylene chloride. The organic phase was dried over sodium sulfate and evaporated to afford an oil, which was chromatographed using methanol/methylene chloride as eluant to afford an oil, which was converted to the hydrochloride salt using HCl in ether, affording the product, 121 mg (48%) as a white solid.

$^1$H-NMR (δ, CDCl$_3$): 1.25 (d, J=6.0 Hz, 6H), 2.6 (m, 12H), 2.8 (m, 4H), 4.44 (m, 6.0 Hz), 4.5 (bs, 2H), 6.36 (d, J=8, 1H), 6.81 (s, 1H), 6.86 (d, J=8, 1H), 7.1–7.3 (m, 6H), 7.40 (t, J=8, 1H), 7.65 (d, J=8, 1H).

$^{13}$C-NMR (δ, CDCl$_3$): 22.16, 33.59, 33.62, 53.13, 53.17, 60.27, 60.53, 71.22, 106.32, 115.53, 115.95, 121.56, 126.05, 128.39, 128.59, 128.70, 131.00, 137.24, 140.27, 141.84, 154.47, 155.33, 158.00.

MS (%): 445 (parent+1, 100).

Anal. Calc'd. for C$_{28}$H$_{36}$N$_4$O.3HCl.3H$_2$O.C$_4$H$_{10}$O: C, 56.34; H, 8.13; N, 8.21. Found: C, 56.00; H, 7.81; N, 8.57.

EXAMPLE 2

6-[2-ISOBUTOXY-4-((4-PHENETHYLPIPERAZIN-1-YL)-ETHYL)-PHENYL]-PYRIDIN-2-YLAMINE

A. 2-Fluoro-4-methylphenylboronic Acid

To a 500 mL three-necked round-bottomed flask equipped with septum and N$_2$ inlet were added 10.0 g (52.9 mmol) 4-bromo-3-fluorotoluene and 100 mL dry tetrahydrofuran. The solution was cooled to –70° C., and 25.4 mL (63.5 mmol) of a 2.5 M solution of butyl lithium in hexane was added slowly so the temperature did not exceed –60° C. The clear solution was stirred at –70° C. for 1 hour, then treated with 10.8 mL (63.5 mmol) triethylborate. The reaction was stirred for 2 hours at –70° C., then warmed to room temperature and stirred for 16 hours. The reaction was quenched with saturated aqueous ammonium chloride solution, adjusted to pH 1–2 with 1 N hydrochloric acid, and extracted with ethyl acetate. The organic layer was washed with brine, dried over sodium sulfate, and evaporated. The residue was triturated with hexane to a white solid, 6.1 g (75%), as a mixture of monoaryl and diaryl boronic acids.

$^1$H-NMR (δ, CDCl$_3$): 2.37 and 2.41 (singlets, 3H), 5.10 (broad doublet for O$\underline{H}$), 6.89 (multiplets, 1H), 7.01 (multiplets, 1H), 7.6–8.0 (multiplets, 1H).

B. N-t-Butylcarbonyl-4-(2-fluoro-4-methylphenyl)-pyridin-2-ylamine

Prepared as in Example 1D in 72.5% yield as an oil.

$^1$H-NMR (δ, CDCl$_3$): 1.33 (s, 9H), 2.38 (s, 3H), 6.955 (d, J=12, 1H), 7.04 (d, J=8, 1H), 7.47 (m, 1H), 7.73 (t, J=8, 1H), 7.79 (t, J=8, 1H), 8.06 (broad s, 1H, N$\underline{H}$), 8.19 (t, J=8, 1H).

$^{13}$C-NMR (δ, CDCl$_3$): 21.1, 27.4, 39.75, 112.255, 116.555, 116.8, 120.1, 120.2, 123.7, 125.1, 130.3, 138.6, 141.3, 151.25, 151.6, 159.0, 161.5, 177.05.

APCI MS (%): 287 (100, parent+1).

C. N-t-Butylcarbonyl-6-(2-isobutoxy-4-methylphenyl)-pyridin-2-ylamine

To a 125 mL three-necked round-bottomed flask equipped with septum, condenser and N$_2$ inlet were added 2.4 mL (26.2 mmol) 2-butanol and 20 mL dry dimethylformamide. The solution was heated to 80° C., and 1.2 g (60% in oil, 30 mmol) sodium hydride was added. The reaction was heated at 80° C. with bubbling for 1 hour, then a solution of 2.5 g (8.7 mmol) N-t-butylcarbonyl-6-(2-fluoro-4-methylphenyl)-pyridin-2-ylamine in 20 mL dry dimethylformamide was added, and the reaction heated at 80° C. for 24 hours. The reaction was cooled, poured into water, and extracted into ethyl acetate. The organic layer was washed thoroughly with water and brine, dried over sodium sulfate, and evaporated. The residue was chromatographed on silica gel using hexane/ethyl acetate as eluant to afford 2.4 g (75%) of the product as an oil.

$^1$H-NMR (δ, CDCl$_3$): 0.90 (t, J=7, 3H), 1.22 (d, J=6, 3H), 1.29 (s, 9H), 1.62 (m, 2H), 2.35 (s, 3H), 4.31 (m, 1H), 6.78

(s, 2H), 6.82 (d, J=8, 1H), 7.58 (m, 1H), 7.67 (t, J=8, 1H), 8.13 (d, J=8, 1H), 8.19 (bs, 1H).

$^{13}$C-NMR (δ, CDCl$_3$): 19.03, 21.52, 27.41, 29.06, 39.66, 75.62, 111.40, 115.25, 121.18, 121.56, 126.73, 130.73, 137.58, 139.97, 150.94, 154.59, 155.44, 176.98.

MS (%): 341 (100, parent+1).

D. 6-[2-Isobutoxy-4-((4-phenethylpiperazin-1-yl)ethyl)-phenyl]-pyridin-2-ylamine The remaining steps in the sequence followed the corresponding steps in Example 1 (E-I) to afford a 63% yield for the final step of product as an oil, which was converted to the hydrochloride salt to give a yellow, amorphous solid.

$^1$H-NMR (δ, CDCl$_3$): 0.90 (t, J=7.5, 3H), 1.21 (d, J=6, 3H), 1.62 (m, 2H), 2.63 (m, 10H), 2.80 (m, 6H), 4.27 (m, 1H), 4.41 (bs, 2H), 6.38 (d, J=8, 1H), 6.80 (s, 1H), 6.86 (d, J=8, 1H), 7.2–7.4 (m, 6H), 7.41 (t, J=8, 1H), 7.65 (d, J=8, 1H).

$^{13}$C-NMR (δ, CDCl$_3$): 9.61, 19.03, 29.04, 33.53, 33.60, 53.09, 53.14, 60.22, 60.46, 75.78, 106.18, 115.34, 115.64, 121.20, 125.96, 128.29, 128.42, 128.61, 130.87, 137.08, 140.22, 141.78, 154.48, 155.42, 157.80.

MS (%): 459 (100, parent+1).

Anal. Calc'd. for $C_{29}H_{38}N_4O·3HCl·1/2H_2O$: C, 60.36; H, 7.34; N, 9.71. Found: C, 60.14; H, 7.53; N 9.33.

EXAMPLE 3

6-[2-ISOBUTOXY-4-((4-DIMETHYLAMINOETHYL)-PHENYL]-PYRIDIN-2-YLAMINE

Prepared as in Example 2, in 13% yield as a hydroscopic hydrochloride salt.

$^1$H-NMR (δ, CDCl$_3$): 0.90 (t, J=7.5, 3H), 1.2–1.3 (m, 6H), 1.63 (m, 2H), 2.305 (s, 3H), 2.55 (m, 2H), 2.76 (m, 2H), 4.28 (m, 1H), 4.38 (bs, 2H), 6.39 (d, J=8, 1H), 6.78 (s, 1H), 6.85 (d, J=8, 1H), 7.21 (d, J=8, 1H), 7.42 (t, J=8, 1H), 7.64 (d, J=8, 1H).

$^{13}$C-NMR (δ, CDCl$_3$): 19.00, 29.04, 29.62, 34.38, 45.35, 61.38, 75.74, 106.18, 115.24, 115.71, 121.16, 128.39, 130.89, 137.11, 141.68, 154.49, 155.42, 157.74.

MS (%): 314 (100, parent+1).

HRMS Calc'd. for $C_{19}H_{28}N_3O$: 314.2232. Found: 314.2231.

EXAMPLE 4

6-[2-CYCLOPENTYLOXY-4-((4-DIMETHYLAMINOETHYL)-PHENYL]-PYRIDIN-2-YLAMINE

Prepared as in Example 2, using cycloopentanol as the starting alcohol in the sodium hydride mediated displacement of the 2-fluoro intermediate in Example 2C, in 36% yield, mp 80° C. (dec.) as the hydrochloride salt.

$^1$H-NMR (δ, CDCl$_3$): 1.55 (m, 2H), 1.68 (m, 2H), 1.81 (m, 4H), 2.29 (s, 6H), 2.53 (m, 2H), 2.75 (m, 2H), 4.41 (bs, 2H), 4.76 (m, 1H), 6.37 (d, J=8, 1H), 6.77 (s, 1H), 6.83 (d, J=8, 1H), 7.17 (d, J=7, 1H), 7.40 (t, J=8, 1H), 7.65 (d, J=8, 1H).

$^{13}$C-NMR (δ, CDCl$_3$): 23.78, 30.22, 32.68, 45.35, 61.39, 79.87, 106.15, 114.55, 115.44, 120.85, 125.43, 130.79, 137.08, 141.69, 154.38, 155.35, 157.82.

MS (%): 326 (100, parent+1).

EXAMPLE 5

6-[2-CYCLOPENTYLOXY-4-((4-PHENETHYLPIPERAZIN-1-YL)-ETHYL)-PHENYL]-PYRIDIN-2-YLAMINE

Prepared as in Example 4, in 60% yield, mp >200° C. as the hydrochloride salt.

$^1$H-NMR (δ, CDCl$_3$): 1.56 (m, 2H), 1.70 (m, 2H), 1.82 (m, 4H), 2.60 (m, 12H), 2.80 (m, 4H), 4.41 (bs, 2H), 4.75 (m, 1H), 6.38 (d, J=8, 1H), 6.80 (s, 1H), 6.84 (d, J=8, 1H), 7.1–7.3 (m, 6H), 7.40 (t, J=8, 1H), 7.65 (d, J=8, 1H).

$^{13}$C-NMR (δ, CDCl$_3$): 23.785, 30.22, 32.70, 33.66, 53.08, 53.11, 60.245, 60.47, 79.865, 106.18, 114.59, 115.45, 120.91, 125.43, 125.97, 128.31, 128.61, 130.77, 137.11, 140.19, 141.74, 154.33, 155.34, 157.80.

MS (%): 471 (100, parent+1).

EXAMPLE 6

6-[2-ISOPROPOXY-(N-(2-METHYL)PROPYL)-4-(PYRROLIDIN-3-YL)-PHENYL]-PYRIDIN-2-YLAMINE

A. N-t-Butylcarbonyl-6-(2-fluoro-4-bromomethylphenyl)-pyridin-2-ylamine

To a 250 mL round-bottomed flask equipped with condenser and N$_2$ inlet were added 5.0 g (17.48 mmol) N-t-butylcarbonyl-6-(2-fluoro-4-methylphenyl)-pyridin-2-ylamine (Example 2B), 4.36 g (24.47 mmol) N-bromosuccinimide, 10 mg azobisdi-(1,1-dimethylcyclohexyl)nitrile, and 85 mL carbon tetrachloride. The reaction was refluxed under a heat lamp for 30 min, cooled, and filtered. The filtrate was concentrated and chromatographed on silica gel using hexane/ethyl acetate as eluant to afford 5.36 g (52%) of the product as an oil, which was crystallized from isopropanol to give mp 97–100° C.

$^1$H-NMR (δ, CDCl$_3$): 1.32 (s, 9H), 4.46 (s, 2H), 7.18 (d, J=11.5, 1H), 7.24 (d, J=8, 1H), 7.49 (d, J=8, 1H), 7.74 (t, J=8, 1H), 7.88 (t, J=8, 1H), 8.06 (bs, 1H), 8.21 (d, J=8, 1H).

$^{13}$C-NMR (δ, CDCl$_3$): 27.52, 31.90, 39.85, 112.92, 116.82, 117.07, 120.37, 120.47, 124.99, 125.03, 126.75, 131.17, 131.20, 138.87, 140.42, 140.51, 150.80, 151.47, 158.99, 161.48, 177.15.

MS (%): 366 (parent+1, 100).

Anal. Calc'd. for $C_{17}H_{18}N_2OFBr$: C, 55.90; H, 4.97; N 7.46. Found: C, 55.57; H, 4.79; N, 7.46.

B. N-t-Butylcarbonyl-6-(2-fluoro-4-formylphenyl)-pyridin-2-ylamine

To a 125 mL round-bottomed flask equipped with condenser and N$_2$ inlet were added 5.35 g (14.66 mmol) N-t-butylcarbonyl-6-2-fluoro4-bromomethylphenyl)-pyridin-2-ylamine, 36 mL chloroform, and 4.10 g (29.32 mmol) hexamethylenetetramine. The reaction was refluxed 5 hours, cooled, and evaporated. The residue was taken up in 29 mL 50% aqueous acetic acid, and refluxed 16 hours. The reaction was cooled, taken up in ethyl acetate, and washed with aqueous sodium hydroxide solution and brine, dried over sodium sulfate and evaporated. The residue was chromatographed on silica gel using hexane/ethyl acetate as eluant to afford 3.49 g (67%) of an oil.

$^1$H-NMR (δ, CDCl$_3$): 1.325 (s, 9H), 7.56 (m, 1H), 7.62 (d, J=11, 1H), 7.7–7.8 (m, 2H), 8.10 (m, 2H), 8.26 (d, J=8, 1H), 9.99 (s, 1H).

$^{13}$C-NMR (δ, CDCl$_6$): 27.41, 39.78, 113.65, 116.41, 116.66, 120.67, 120.77, 125.66, 131.63, 137.84, 138.93, 149.83, 151.60, 159.35, 161.86, 177.14, 190.54.

MS (%): 301 (parent+1, 100).

Anal. Calc'd. for $C_{17}H_{17}N_2O_2F$: C, 67.99; H, 5.71; N, 9.33. Found: C, 67.62; H, 5.67; N, 9.50.

C. Diethyl-2-fluoro-4-[N-t-butylcarbonyl-6-pyridin-2-ylamine]benzylidenemalonate To a 125 mL round-bottomed flask equipped with N$_2$ inlet were added 2.65 g (8.83 mmol) N-t-butylcarbonyl-6-(2- fluoro-4-formylphenyl)-pyridin-2-ylamine, 1.41 9 (8.83 mmol) diethyl malonate, 45 mL benzene, 40 mg (0.44 mmol) piperidine, and 10 mg benzoic acid. The reaction was refluxed 3 days, cooled, and poured into water and ethyl acetate. The organic layer was washed with 1N hydrochloric acid, aqueous sodium bicarbonate solution, and brine, dried over sodium sulfate, and evaporated. The residue was chromatographed on silica gel using hexane/ethyl acetate as eluant to afford the product as a yellow oil, 3.14 g (80%), which was crystallized from 2-propanol, mp 97–100° C.

$^1$H-NMR ($\delta$, CDCl$_3$): 1.32 (m, 15H), 4.29 (q, J=7, 2H), 4.34 (q, J=7, 2H), 7.24 (d, J=12, 1H), 7.32 (d, J=8, 1H), 7.53 (d, J=7, 1H), 7.67 (s, 1H), 7.75 (t, J=8, 1H), 7.96 (t, J=8, 1H), 8.05 (bs, 1H), 8.22 (d, J=8, 1H).

$^{13}$C-NMR ($\delta$, CDCl$_3$): 13.94, 14.12, 27.51, 39.85, 61.89, 61.97, 113.27, 116.75, 117.00; 120.53, 120.63, 125.63, 125.66, 127.77, 131.10, 131.13, 135.09, 135.17, 138.95, 139.89, 150.29, 151.53, 159.04, 161.55, 163.76, 166.20, 177.16.

MS (%): 443 (parent+1, 100).

Anal. Calc'd. for C$_{24}$H$_{27}$N$_2$O$_5$F: C 65.15; H, 6.15; N, 6.33. Found: C, 64.88; H, 6.18; N, 6.59.

D. Ethyl-3-[2-fluoro-4-(N-t-butylcarbonyl-6-pyridin-2-ylamine)]phenyl-3-cyano-propionate To a 125 mL round-bottomed flask equipped with condenser and N$_2$ inlet were added 3.12 mg (7.05 mmol) diethyl-2-fluoro-4-[N-t-butylcarbonyl-6-pyridin-2-ylamine] benzylidenemalonate and 100 mL ethanol. To the stirring solution was added a solution of 460 mg (7.05 mmol) potassium cyanide in 1.8 mL water, and the reacton stirred at room temperature for 3 days, then heated for 38 hours at 60° C. The reaction was cooled and quenched with dilute hydrochloric acid, then taken up in ethyl acetate and washed with acid and brine, dried over sodium sulfate, and evaporated. The residue was chromatographed on silica gel using hexane/ethyl acetate as eluant to afford 1.88 g (67%) of an oil.

$^1$H-NMR ($\delta$, CDCl$_3$): 1.24 (t, J=7, 3H), 1.32 (s, 9H), 2.93 (AB$_q$, J=8, $\Delta\nu$=58, 2H), 4.17 (m, 2H), 4.33 (t, J=7, 1H), 7.19 (d, J=11, 1H), 7.26 (d, J=8, 1H), 7.48 (m, 1H), 7.75 (t, J=8, 1H), 7.94 (t, J=8, 1H), 8.05 (bs, 1H), 8.225 (d, J=8, 1H).

$^{13}$C-NMR ($\delta$, CDCl$_3$): 14.0, 27.4, 32.5, 39.6, 39.8, 61.6, 113.0, 115.4, 115.7, 119.2, 120.6, 123.4, 127.6, 127.7, 131.7, 137.0, 138.9, 150.3, 151.4, 159.1, 161.6, 168.7, 177.1.

MS (%): 398 (parent+1, 100).

E. N-t-Butylcarbonyl-6-[2-fluoro-4-(2-oxo-pyrrolidin-3-yl)-phenyl]-pyridin-2-ylamine To a 125 mL Paar bottle were added 1.88 g (4.73 mmol) ethyl-3-[2-fluoro-4-(N-t-butylcarbonyl-6-pyridin-2-ylamine)]phenyl-3-cyano-propionate, 35 mL ethanol, 1 g 10% palladium-on-carbon and 2 mL 6 N hydrochloric acid. The reaction was shaken under 40 p.s.i. hydrogen for 20 hours, filtered through Celite, and the filtrate evaporated. The residue was taken up in ethyl acetate, washed with aqueous sodium hydroxide, dried over sodium sulfate, and evaporated. The residue was taken up in 35 mL dry toluene, treated with 3.5 mL triethylamine, and heated at reflux for 18 hours. The reaction was then cooled, washed with dilute aqueous hydrochloric acid and brine, dried over sodium sulfate, and evaporated. The residue was chromatographed on silica gel using hexane/ethyl acetate as eluant to afford 394 mg (23%) of a solid, mp 162–165° C.

$^1$H-NMR ($\delta$, CDCl$_3$): 1.31 (s, 9H), 2.59 (AB$_q$, J=8, $\Delta\nu$=112, 2H), 3.27 (m, 1H), 3.68 (m, 2H), 7.01 (d, J=12, 1H), 7.10 (d, J=8, 1H), 7.19 (s, 1H), 7.44 (m, 1H), 7.73 (t, J=8, 1H), 7.84 (t, J=8, 1H), 8.20 (d, J=8, 1H), 8.23 (bs, 1H).

$^{13}$C-NMR ($\delta$, CDCl$_3$): 27.465, 37.8, 39.6, 39.9, 49.2, 112.9, 114.6, 114.8, 120.2, 120.3, 122.7, 125.6, 128.2, 129.0, 131.3, 138.9, 145.7, 150.9, 151.6, 15.2, 161.7, 177.3, 177.5.

MS (%): 356 (parent+1, 100).

Anal. Calc'd. for C$_{20}$H$_{22}$N$_3$O$_2$F: C, 67.59; H, 6.24; N, 11.82. Found: C, 67.49; H, 6.37; N, 11.76.

F. 6-[2-Fluoro-4-(2-oxo-pyrrolidin-3-yl)-phenyl]-pyridin-2-ylamine

The above material was deblocked using 6 N hydrochloric acid at 90° C. for 18 hours followed by treatment with N-ethyl,N-isopropylcarbodiimide and N-hydroxybenztriazole with triethylamine and 4-dimethylaminopyridine in acetonitrile at room temperature for 2 days. The reaction was worked up with ethyl acetate and water, dried over sodium sulfate, and evaporated. The residue was chromatographed on silica gel using methanol/methylene chloride as eluant to afford a solid, mp 185–188° C., 167 mg (47%).

$^1$H-NMR ($\delta$, CDCl$_3$): 2.49 (AB$_q$, J=8, $\Delta\nu$=108, 2H), 3.22 (m, 1H), 3.60 (m, 2H), 4.90 (bs, 2H), 6.38 (d, J=8, 1H), 6.87 (m, 2H), 6.97 (d, J=8, 1H), 7.35 (t, J=8, 1H), 7.59 (t, J=8, 1H).

$^{13}$C-NMR ($\delta$, CDCl$_3$): 37.6, 39.3, 49.1, 108.0, 114.1, 114.4, 122.4, 126.3, 131.0, 138.2, 144.6, 150.6, 158.6, 158.8, 161.3, 177.9.

MS (%): 272 (parent+1, 100).

G. 6[-2-Fluoro-4-(pyrrolidin-3-yl)-phenyl]-pyridin-2-ylamine

To a 25 mL round-bottomed flask equipped with N$_2$ inlet were added 160 mg (0.59 mmol) 6-[2-fluoro-4-(2-oxo-pyrrolidin-3-yl)-phenyl]-pyridin-2-ylamine and 8 mL dry tetrahydrofuran. The solution was cooled to –70° C., and 5.9 mL (5.9 mmol) of a 1.0 M solution was lithium aluminum hydride in tetrahydrofuran was added. The reaction was warmed to room temperature and stirred 2 days. The reaction was carefully quenched with dilute aqueous sodium hydroxide solution, then taken up in ethyl acetate and aqueous sodium hydroxide solution, and the combined organic layer washed with water, dried over sodium sulfate, and evaporated to afford a crude oil, which was used directly in the next step.

$^1$H-NMR ($\delta$, CDCl$_3$): 1.8–2.0 and 2.2–2.4 (m, 2H), 2.6–3.7 (m, 5H), 4.80 (bs, 2H), 6.41 (d, J=8, 1H), 6.92 (m, 2H), 7.01 (d, J=8, 1H), 7.21 (d, J=8, 1H), 7.395 (t, J=8, 1H), 7.66 (t, J=8, 1H), 7.71 (m, 1H).

MS (%): 258 (100, parent+1)

H. 6-[2-Fluoro-(N-(2-methyl)propyl)4-(pyrrolidin-3-yl)-phenyl]-pyridin-2-ylamine To a 25 mL round-bottomed flask equipped with N$_2$ inlet were added 151 mg (0.587 mmol) 6-[2-fluoro-4-(pyrrolidin-3-yl)-phenyl]-pyridin-2-ylamine, 85 mg (1.175 mmol) isobutyraldehyde, 74 mg (1.175 mmol) sodium cyanoborohydride, and 6 mL methanol. The reaction was stirred at room temperature for 2 hours, poured into dilute hydrochloric acid, and washed with ethyl acetate. The aqueous layer was adjusted to pH 12 with 1 N aqueous sodium hydroxide solution and extracted with ethyl acetate. The organic layer was dried over sodium sulfate and evaporated, and the residue chromatographed on silica gel using methanol/methylene chloride to afford 25 mg (%) of an oil.

$^1$H-NMR ($\delta$, CDCl$_3$): 0.94 (d, J=6, 6H), 1.7–1.9 (m, 2H), 2.32 (m, 3H), 2.55 (m, 1H), 2.74 (m, 2H), 2.98 (m, 1H), 3.37 (m, 1H), 4.49 (bs, 2H), 6.44 (d, J=8, 1H), 7.05 (d, J=12, 1H), 7.11 (m, 2H), 7.46 (t, J=8, 1H), 7.79 (t, J=8, 1H).

$^{13}$C-NMR ($\delta$, CDCl$_3$): 21.0, 27.2, 33.0, 42.7, 54.7, 61.9, 64.7, 107.2, 114.6, 114.7, 123.2, 125.4, 130.5, 137.9, 148.4, 151.6, 158.1, 159.0, 161.5.

MS (%): 314 (parent+1, 100).

I. 6-[2-isopropoxy-(N-(2-methyl)propyl)-4-(pyrrolidin-3-yl)-phenyl]-pyridin-2-ylamine To a 25 mL round-bottomed flask equipped with condenser and $N_2$ inlet were added 24 mg (0.077 mmol) 6-[2-fluoro-(N-(2-methyl)propyl)-4-(pyrrolidin-3-yl)-phenyl]-pyridin-2-ylamine and 3 mL dry dimethylformamide. The solution was heated to 80° C., and 46 mg (0.767 mmol) 2-propanol and 37 mg (0.920 mmol) sodium hydride (60% dispersion in oil) were added. The reaction was stirred at 100° C. for 18 hours, then cooled and evaporated. The residue was treated with dioxane and 1 N aqueous sodium hydroxide solution to cleave some N-formylated byproduct at room temperature for 18 hours. The reaction was partitioned between 0.5 N aqueous sodium hydroxide solution and ethyl acetate, and the organic layer washed with brine, dried over sodium sulfate, and evaporated. The residue was chromatographed by preparative plate silica gel chromatography using methanol/methylene chloride/ammonia as eluant to afford 24 mg (89%) of an oil, which was converted to the hydrochloride salt, mp 118–138° C.

$^1$H-NMR ($\delta$, CDCl$_3$): 0.96 (d, J=7, 6H), 1.25 (d, J=6, 6H), 1.8 (m, 1H), 1.9 (m, 1H), 2.4 (m, 3H), 2.64 (m, 1H), 2.85 (m, 2H), 3.07 (m, 1H), 3.38 (m, 1H), 4.45 (m, 3H), 6.395 (d, J=8, 1H), 6.92 (m, 2H), 7.22 (t, J=8, 1H), 7.42 (t, J=7, 1H), 7.64 (d, J=8, 1H).

$^{13}$C-NMR ($\delta$, CDCl$_3$): 21.0, 22.2, 27.2, 33.1, 43.2, 55.0, 62.0, 64.75, 71.2, 106.4, 114.5, 115.6, 119.9, 128.7, 131.0, 137.3, 146.4, 154.4, 155.4, 157.9.

MS (%): 354 (parent+1, 100).

EXAMPLE 7

1-[4-(6-AMINO-PYRIDIN-2-YL)-3-ISOPROPOXY-PHENYL]-2-(4-PHENETHYL-PIPERAZIN-1-YL)-ETHANOL

A. N-t-Butylcarbonyl6-(2-isopropoxy-4-formylphenyl)-pyridin-2-ylamine

To a 100 mL round-bottomed flask equipped with condenser and $N_2$ inlet were added 4.85 g (11.97 mmol) N-t-butylcarbonyl-6-(2-isopropoxy-4-bromomethylphenyl)-pyridin-2-ylamine (from Example 1E above), 3.35 g (23.95 mmol) hexamethylene tetramine, and 30 mL chloroform, and the reaction refluxed for 2 hours. The reaction was concentrated and taken up in 24 mL of 1:1 acetic acid:water and refluxed for 5 hours. The reaction was cooled, adjusted to pH 10 with aqueous sodium hydroxide solution, and extracted into ethyl acetate. The organic phase was washed with brine, dried over sodium sulfate, and evaporated. The residue was chromatographed on silica gel using hexane/ethyl acetate as eluant to afford 2.995 g (74%) of a white solid.

$^1$H-NMR ($\delta$, CDCl$_3$): 1.32 (m, 15H), 4.68 (septet, J=6, 1H), 7.47 (s, 1H), 7.51 (d, J=8, 1H), 7.64 (m, 1H), 7.72 (t, J=8, 1H), 7.90 (d, J=8, 1H), 8.05 (bs, 1H), 8.20 (d, J=8, 1H), 9.99 (s, 1H).

MS (%): 341 (parent+1, 100).

B. N-t-Butylcarbonyl-6-(2-isopropoxy-4-oxiranylphenyl)-pyridin-2-ylamine

To a 100 mL round-bottomed flask equipped with condenser and $N_2$ inlet were added 2.99 g (8.79 mmol) N-t-butylcarbonyl-6-(2-isopropoxy-4-formylphenyl)-pyridin-2-ylamine, 1.79 g (8.79 mmol) trimethylsulfonium iodide, 0.98 9 (17.59 mmol) powdered potassium hydroxide, 44 mL acetonitrile, and 0.5 mL water. The reaction was heated to 60° C. for 2.5 hours, then cooled, filtered, and evaporated. The yellow oil was used directly, 3.3 g (~100%).

$^1$H-NMR ($\delta$, CDCl$_3$): 1.27 (d, J=6, 6H), 1.32 (s, 9H), 2.76 (m, 1H), 3.15 (m, 1H), 3.87 (m, 1H), 4.54 (septet, 1H), 6.87 (s, 1H), 6.97 (d, J=8, 1H), 7.58 (m, 1H), 7.69 (m, 2H), 8.05 (bs, 1H), 8.13 (d, J=8, 1H).

MS (%): 355 (parent+1, 100).

C. 1-[N-t-Butylcarbonyl-4-(6-amino-pyridin-2-yl)-3-isopropoxy-phenyl]-2-(4-phenethyl-piperazin-1-yl)-ethanol To a 25 mL round-bottomed flask equipped with condenser and $N_2$ inlet were added 300 mg (0.847 mmol) N-t-butylcarbonyl-6-(2-isopropoxy-4-oxiranylphenyl)-pyridin-2-ylamine, 193 mg (1.017 mmol) N-phenethylpiperazine, 9 mL acetonitrile, and 0.85 mL water. The reaction was heated to 80° C. for 20 hours, cooled, and partitioned between ethyl acetate and aqueous sodium bicarbonate. The organic phase was separated, washed with brine, dried over sodium sulfate, and evaporated. The residue was chromatographed on silica gel using methanol/methylene chloride/ammonium hydroxide as eluant to afford 283 mg (62%) of an off-white foam.

$^1$H-NMR ($\delta$, CDCl$_3$): 1.27 (d, J=6, 6H), 1.31 (s, 9H), 2.4–2.9 (m, 15H), 4.56 (septet, J=6, 1H), 4.75 (m, 1H), 6.99 (d, J=8, 1H), 7.06 (s, 1H), 7.1–7.3 (m, 5H), 7.58 (d, J=8, 1H), 7.67 (m, 2H), 8.08 (bs, 1H), 8.13 (d, J=8, 1H).

$^{13}$C-NMR ($\delta$, CDCl$_3$): 22.05, 27.45, 33.53, 39.71, 53.18, 60.36, 65.95, 68.41, 70.99, 111.54, 112.10, 118.26, 121.18, 126.01, 128.34, 128.61, 130.80, 137.67, 140.09, 144.34, 150.98, 154.29, 155.47, 176.99.

MS (%): 545 (parent+1, 100).

D. 1-4-(6-Amino-pyridin-2-yl)-3-isopropoxy-phenyl-2-(4-phenethyl-piperazin-1-ethanol To a 25 mL round-bottomed flask equipped with condenser and $N_2$ inlet were added 283 mg (0.52 mmol) 1-[N-t-butylcarbonyl-4-(6-amino-pyridin-2-yl)-3-isopropoxy-phenyl]-2-(4-phenethyl-piperazin-1-yl)-ethanol, 5 mL dioxane, and 10 mL 10% aqueous sodium hydroxide solution. The reaction was refluxed 3 days, cooled, poured into water, and extracted into ethyl acetate. The organic phase was washed with brine, dried over sodium sulfate, and evaporated. The residue was chromatographed on silica gel using methanoimethylene chloride/ammonium hydroxide as eluant to afford 203 mg (86%) of an oil, which was converted to the hydrochloride salt using HCl in tetrahydrofuran, mp 148–165° C.

$^1$H-NMR ($\delta$, CDCl$_3$): 1.27 (d, J=6, 6H), 2.6–2.9 (m, 15H), 4.48 (bs, 2H), 4.52 (septet, J=6, 1H), 4.74 (m, 1H), 6.385 (d, J=8, 1H), 6.97 (d, J=8, 1H), 7.03 (s, 1H), 7.1–7.3 (m, 6H), 7.41 (t, J=8, 1H), 7.70 (d, J=8, 1H).

$^{13}$C-NMR ($\delta$, CDCl$_3$): 22.16, 33.62, 53.03, 53.27, 60.45, 66.04, 68.57, 71.19, 106.47, 112.56, 115.62, 118.46, 126.09, 128.42, 128.70, 129.75, 130.97, 137.27, 140.22, 143.81, 154.35, 155.52, 158.01.

MS (%): 461 (parent+1, 100).

Anal. Calc'd. for $C_{28}H_{36}N_4O_2 \cdot 3HCl \cdot 2H_2O$: C, 55.49; H, 7.15; N, 9.24. Found: C, 55.50; H, 7.38; N, 8.97.

What is claimed is:
1. A compound of the formula

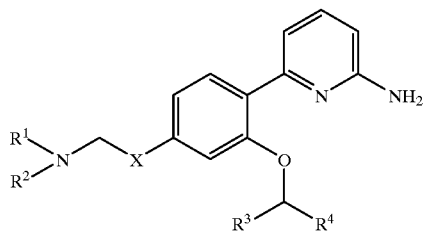

I wherein X is CHOH or $CH_2$;

$R^1$, $R^2$, $R^3$ and $R^4$ are selected, independently, from $(C_1–C_6)$alkyl, tetrahydronaphthalene, aryl and aralkyl, wherein said aryl and the moiety of said aralkyl is phenyl or naphthyl and the alkyl moiety is straight or branched and contains from 1 to 6 carbon atoms, and wherein said $(C_1–C_6)$ alkyl and said tetrahydronaphthalene and the aryl moiety of said aralkyl may optionally be substituted with from one to three substituents, preferably from zero to two substituents, that are selected, independently, from halo (e.g. chloro, fluoro, bromo, iodo), nitro, hydroxy, cyano, amino, $(C_1–C_4)$ alkoxy, and $(C_1–C_4)$ alkylamino;

or $R^1$ and $R^2$, together with the nitrogen to which they are attached, form a piperazine, piperidine or pyrrolidine ring or an azabicyclic ring containing from 6 to 14 ring members, from 1 to 3 of which are nitrogen and the rest of which are carbon;

and wherein said piperazine, piperidine and pyrrolidine rings may optionally be substituted with one or more substituents, preferably with from zero to two substituents that are selected, independently, from $(C_1–C_6)$ alkyl, amino, $(C_1–C_6)$ alkylamino, amino, phenyl substituted 5 to 6 membered heterocyclic rings containing from 1 to 4 ring nitrogen atoms, benzoyl, benzoylmethyl, benzylcarbonyl, phenylaminocarbonyl, phenylethyl and phenoxycarbonyl, and wherein the phenyl moieties of any of the foregoing substituents may optionally be substituted with one or more substituents, preferably with from zero to two substituents, that are selected, independently, from halo, $(C_1–C_3)$alkyl, $(C_1–C_3)$alkoxy, nitro, amino, cyano, $CF_3$ and $OCF_3$;

and the pharmaceutically acceptable salts of such compound.

2. A compound according to claim 1, wherein $R^1$ and $R^2$, together with the nitrogen to which they are attached, form a ring selected from

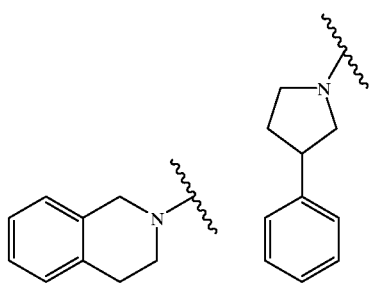

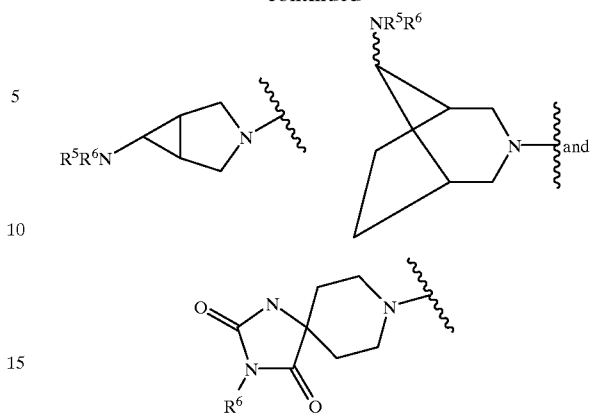

wherein $R^5$ and $R^6$ are selected from hydrogen, $(C_1–C_6)$ alkyl, phenyl, naphthyl, $(C_1–C_6)$alkyl-C(=O)—, HC(=O)—, $(C_1–C_6)$alkoxy-(C=O)—, phenyl-C (=O)—, naphthyl-C(=O)—, and $R^8R^9NC(=O)$— wherein $R^8$ and $R^9$ are selected, independently, from hydrogen and $(C_1–C_6)$alkyl; and $R^7$ is selected from hydrogen, $(C_1–C_6)$alkyl, phenyl, naphthyl, phenyl$(C_1–C_6)$alkyl- end naphthyl$(C_1–C_6)$ alkyl-.

3. A compound according to claim 1, wherein $R^1$ and $R^2$, together with the nitrogen to which they are attached, form an optionally substituted piperidine, piperazine pyrrolidine, or 3-aza-bicyclo[3.1.0]hex-6-ylamine ring.

4. A compound according to claim 1, $R^3$ and $R^4$, together with the carbon to which they are attached, form an optionally substituted carbocyclic ring of from 3 to 8 members.

5. A pharmaceutical composition for treating or preventing a condition selected from the group consisting of migraine, inflammatory diseases, asthma, psoriasis, stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, Parkinson's disease, chemical dependencies and addictions, emesis, epilepsy, anxiety, psychosis, depression, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, glaucoma, macular degeneration, diabetic neuropathy, diabetic nephropathy and cancer in a mammal, comprising an amount of a compound according to claim 1 that is effective in treating or preventing such condition and a pharmaceutically acceptable carrier.

6. A pharmaceutical composition for inhibiting nitric oxide synthase (NOS) in a mammal, according to claim 1, comprising a NOS inhibiting effective amount of a compound according to claim 1, and a pharmaceutically acceptable carrier.

7. A pharmaceutical composition for treating or preventing a condition selected from the group consisting of migraine, inflammatory diseases, asthma, psoriasis, stroke, acute and chronic pain, hypovolemic shock, traumatic shock, reperfusion injury, Crohn's disease, ulcerative colitis, septic shock, multiple sclerosis, AIDS associated dementia, neurodegenetative diseases, neuron toxicity, Alzheimer's disease, Parkinson's disease, chemical dependencies and addictions, emesis, epilepsy, anxiety, psychosis, depression, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, glaucoma, macular degeneration, diabetic neuropathy, diabetic nephropathy and cancer in a mammal, comprising a NOS inhibiting effective amount of a compound according to claim 1 and a pharmaceutically acceptable carrier.

8. A method of inhibiting NOS in a mammal, comprising administering to said mammal a NOS inhibiting effective amount of a compound according to claim 1.

9. A method of treating or preventing a condition selected from the group consisting of migraine, inflammatory diseases, asthma, psoriasis, stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, Parkinson's disease, chemical dependencies and addictions, emesis, epilepsy, anxiety, psychosis, depression, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spina cord injury, Huntington's disease, glaucoma, macular degeneration, diabetic neuropathy, diabetic nephropathy and cancer in a mammal, comprising administering to said mammal a NOS inhibiting effective amount of a compound according to claim 1.

* * * * *